United States Patent [19]

Rajagopalan

[11] 4,238,607
[45] Dec. 9, 1980

[54] PYRIDOPYRROLO BENZHETEROCYCLES

[75] Inventor: Parathasarathi Rajagopalan, Wilmington, Del.

[73] Assignee: Endo Laboratories Inc., Garden City, N.Y.

[21] Appl. No.: 55,701

[22] Filed: Jul. 9, 1979

Related U.S. Application Data

[60] Division of Ser. No. 916,846, Jun. 16, 1978, Pat. No. 4,183,936, which is a division of Ser. No. 755,121, Dec. 28, 1976, Pat. No. 4,115,577, which is a division of Ser. No. 586,746, Jun. 13, 1975, Pat. No. 4,013,652, which is a division of Ser. No. 357,528, May 7, 1973, Pat. No. 3,914,421, which is a continuation-in-part of Ser. No. 263,766, Jun. 19, 1972, abandoned.

[51] Int. Cl.$^3$ ............................................. C07D 471/14
[52] U.S. Cl. ..................................... 544/14; 424/246; 544/99
[58] Field of Search ........................................ 544/14

[56] References Cited

U.S. PATENT DOCUMENTS

| 4,013,652 | 3/1977 | Rajagopalan | 544/14 |
| 4,115,577 | 9/1978 | Rajagopalan | 544/14 |

Primary Examiner—John M. Ford

[57] ABSTRACT

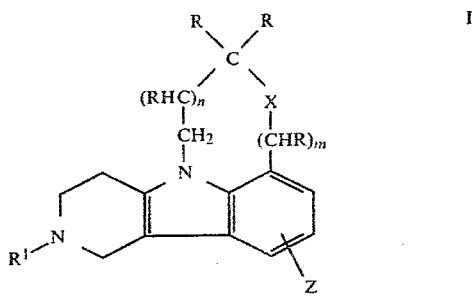

where X is O, S, S→O, or SO$_2$; n is 0 or 1; m is 0 or 1; the R's are the same or different and are H or CH$_3$, and one of them can be C$_2$–C$_9$ alkyl, phenyl, C$_7$–C$_{10}$ phenylalkyl, furyl, thienyl, pyridyl or substituted phenyl or phenylalkyl; when X is S, and m is 0, one R in the group —RCR— can be OCH$_3$; when X is S and m is 1, the R in the group (CHR)$_m$ can be OCH$_3$; and R$^1$ is H, C$_1$–C$_4$ alkyl, C$_3$–C$_5$ alkenyl, C$_3$–C$_5$ alkynyl, C$_3$–C$_6$ cycloalkyl, C$_2$–C$_4$ alkoxycarbonyl, trifluoroacetyl, or substituted C$_1$–C$_4$ alkyl where the substituent is C$_3$–C$_6$ cycloalkyl, phenyl or substituted phenyl; and their pharmaceutically suitable salts. The compounds are useful as sedatives; some of them also exhibit antidepressant, antihypertensive and antibacterial activity.

The compounds are prepared by cyclizing compounds of formula II

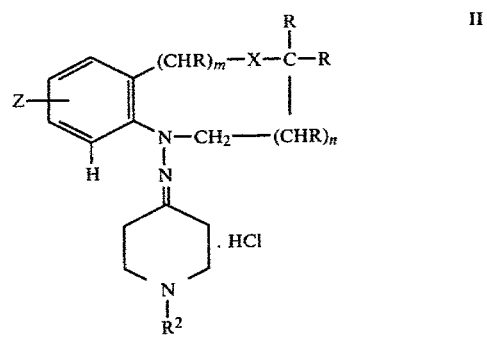

wherein R$^2$ is R$^1$ or acyl. The latter compounds are prepared by reacting 4-piperidones with compounds of formula III in the presence of a reducing agent

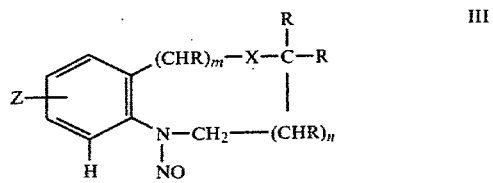

or with compounds of formula VI

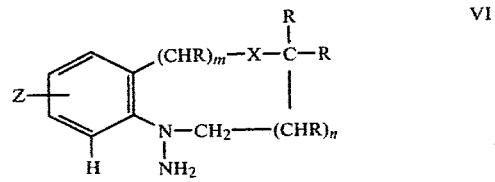

2 Claims, No Drawings

PYRIDOPYRROLO BENZHETEROCYCLES

CROSS REFERENCE TO RELATED APPLICATION

This is a Ser. No. 916,846, filed June 16, 1978, now U.S. Pat. No. 4,183,936 which is a division of Application Ser. No. 755,121, filed Dec. 28, 1976, now U.S. Pat. No. 4,115,577; which in turn is a division of Application Ser. No. 586,746, filed June 13, 1975, now U.S. Pat. No. 4,013,652; which in turn is a division of Application Ser. No. 357,528, filed May 7, 1973, now U.S. Pat. No. 3,914,421; which is a continuation-in-part of Application Ser. No. 263,766, filed June 19, 1972, now abandoned.

BACKGROUND OF THE INVENTION

This invention relates to novel pyrido[3',4':4,5]-pyrrolo[1,2,3-ef][1,5]benzothiazepines and -benzoxazepines, novel pyrido[3',4':4,5]pyrrolo[1,2,3-de][1,4]benzothiazines and -benzoxazines, novel pyrido[3',4':4,5-]pyrrolo[3,2,1-jk][4,1]benzothiazepines and -benzoxazepines, novel pyrido[3',4':4,5]pyrrolo[3,2,1-kl][5,1]benzothiazocines and -benzoxazocines, and novel intermediates therefor.

U.S. Pat. No. 3,299,078 discloses pyrido[3',4':4,5]pyrrolo[3,2,1-hi]indole and -[3,2,1-ij]quinoline of the formula:

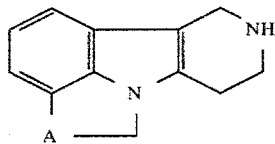

where A is methylene or ethylene, and certain substituted derivatives thereof. According to the disclosure, the compounds have analgesic, anti-pyretic, anti-inflammatory, anti-serotonin, and CNS stimulant activity. The patent also discloses intermediates having the formula:

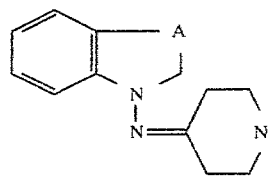

where A is methylene or ethylene, and cyclization of these intermediates to form the pyridopyrroloindoles and -quinolines.

SUMMARY OF THE INVENTION

This invention is a class of novel compounds having the formula:

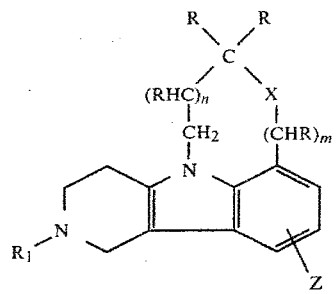

where
X is O, S,

or $SO_2$;
n is 0 or 1;
m is 0 or 1;
the R's are the same or different and are H or $CH_3$, and one of them can be $C_2$–$C_9$ alkyl, phenyl, $C_7$–$C_{10}$ phenylalkyl, furyl, thienyl, pyridyl, phenyl or $C_7$–$C_{10}$ phenylalkyl substituted on adjacent ring carbon atoms with methylenedioxy, or phenyl or $C_7$–$C_{10}$ phenylalkyl substituted on the ring with 1, 2 or 3 substituents individually selected from methoxy, ethoxy, bromine, chlorine, fluorine, trifluoromethyl and $C_1$–$C_4$ alkyl; when X is S and m is 0 one R on the group —RCR— can be —$OCH_3$; and when X is S and m is 1, the R on the group $(CHR)_m$ can be —$OCH_3$.
$R^1$ is hydrogen, $C_1$–$C_4$ alkyl, $C_3$–$C_5$ alkenyl, $C_3$–$C_5$ alkynyl, $C_3$–$C_6$ cycloalkyl, $C_2$–$C_4$ alkoxycarbonyl, trifluoroacetyl or substituted $C_1$–$C_4$ alkyl where the substituent is $C_3$–$C_6$ cycloalkyl, phenyl, phenyl substituted on adjacent carbon atoms with methylenedioxy, or phenyl substituted with 1, 2 or 3 substituents individually selected from methoxy, ethoxy, bromine, chlorine, fluorine, trifluoromethyl and $C_1$–$C_4$ alkyl; and
Z is H, Cl or $CH_3$;
and their pharmaceutically suitable salts.

The compounds are useful as sedatives. Some of the compounds also have antidepressant, antihypertensive and antibacterial activity.

The invention includes the novel intermediates of formulae II, III, and VI and the process of making the compounds of formula I by cyclization of compounds of formula II as described hereinbelow.

The invention also includes pharmaceutical preparations containing the compounds of formula I and their pharmaceutically suitable salts, and methods of producing sedation in warm-blooded animals by administration thereof.

DESCRIPTION OF THE INVENTION

Nomenclature

Formula I encompasses eight novel ring systems:

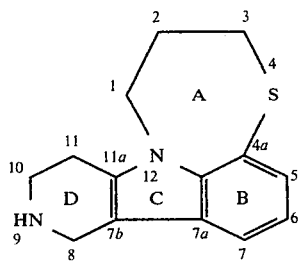

2,3,8,9,10,11-hexahydro-1H-pyrido[3',4':4,5]pyrrolo[1,2,3-ef][1,5]benzothiazepine

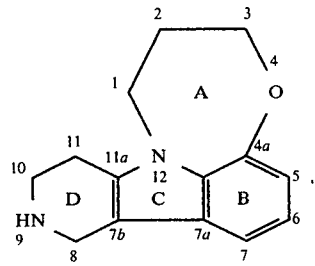

2,3,8,9,10,11-hexahydro-1H-pyrido[3',4':4,5]pyrrolo[1,2,3-ef][1,5]benzoxazepine

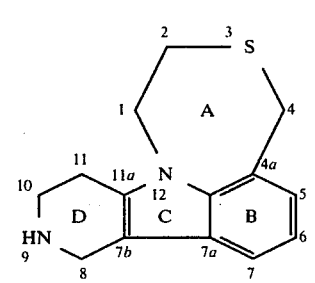

1,2,7,8,9,10-hexahydropyrido[3',4':4,5]pyrrolo[1,2,3-de][1,4]benzothiazine

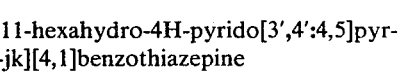

1,2,7,8,9,10-hexahydropyrido[3',4':4,5]pyrrolo[1,2,3-de][1,4]benzoxazine

Ie 1,2,8,9,10,11-hexahydro-4H-pyrido[3',4':4,5]pyrrolo[3,2,1-jk][4,1]benzothiazepine

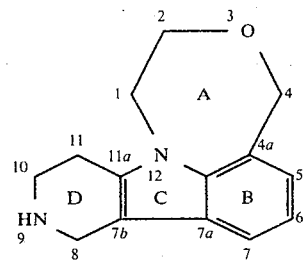

1,2,8,9,10,11-hexahydro-4H-pyrido[3',4':4,5]pyrrolo[3,2,1-jk][4,1]benzoxazepine

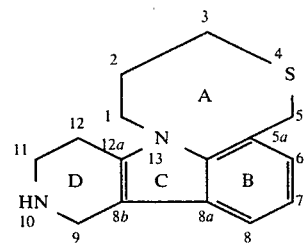

2,3,9,10,11,12-hexahydro-1H,5H-pyrido[3',4':4,5]pyrrolo[3,2,1-kl][5,1]benzothiazocine

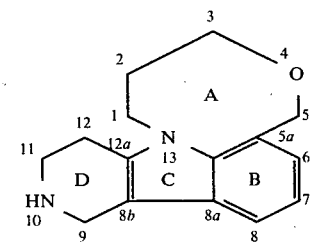

2,3,9,10,11,12-hexahydro-1H,5H-pyrido[3',4':4,5]pyrrolo[3,2,1-kl][5,1]benzoxazocine In formulae Ia-Ih, rings C and D constitute the pyrrole and pyridine rings, respectively. Rings A and B together constitute the 1,5-benzothiazepine system in Ia, the 1,5-benzoxazepine system in Ib, the 1,4-benzothiazine system in Ic, the 1,4-benzoxazine system in Id, the 4,1-benzothiazepine system in Ie, the 4,1-benzoxazepine system in If, the 5,1-benzothiazocine system in Ig, and the 5,1-benzoxazocine system in Ih.

The corresponding intermediates of formula II are named as follows:

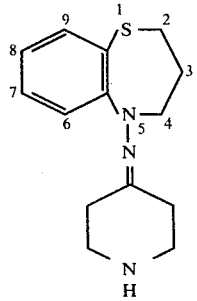 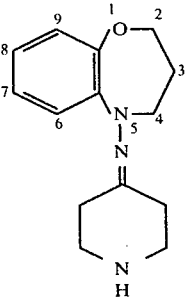

IIa IIb

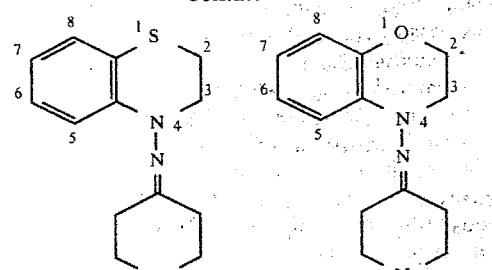
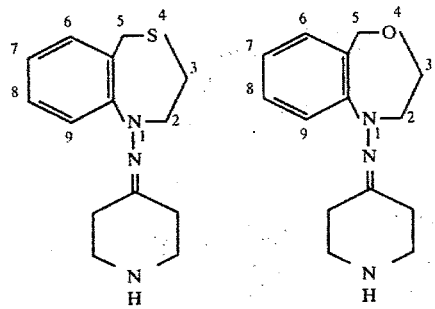
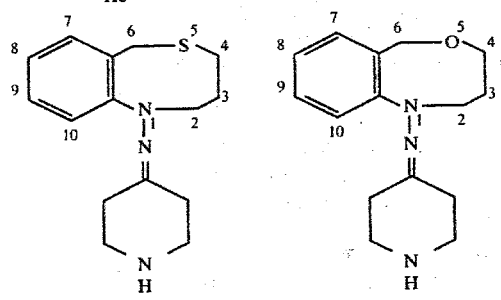

IIa: 2,3,4,5-tetrahydro-5[(4-piperidylidene)amino]-1,5-benzothiazepine

IIb: 2,3,4,5-tetrahydro-5[(4-piperidylidene)amino]-1,5-benzoxazepine

IIc: 3,4-dihydro-2H-4[(4-piperidylidene)amino]-1,4-benzothiazine

IId: 3,4-dihydro-2H-4[(4-piperidylidene)amino]-1,4-benzoxazine

IIe: 1,2,3,5-tetrahydro-1[(4-piperidylidene)amino]-4,1-benzothiazepine

IIf: 1,2,3,5-tetrahydro-1[(4-piperidylidene)amino]-4,1-benzoxazepine

IIg: 1,3,4,6-tetrahydro-1[(4-piperidylidene)amino]-2H-5,1-benzothiazocine

IIh: 1,3,4,6-tetrahydro-1[(4-piperidylidene)amino]-2H-5,1-benzoxazocine

Synthesis

Compounds of Formula I

Compounds of Formula I are prepared simply by heating, to a temperature in the range of about 60° C. to about 200° C., a compound of formula II, preferably in the form of its hydrochloride salt, in a solvent, as shown in reaction scheme A:

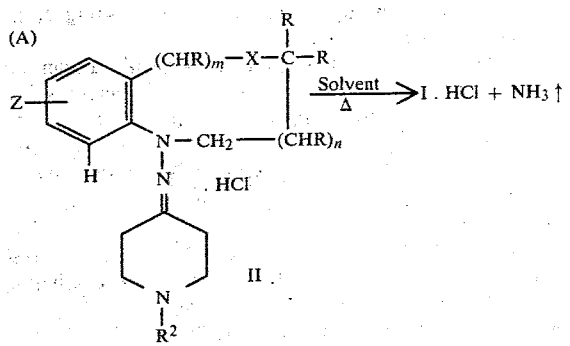

where $R^2$ is $R^1$, formyl, $C_2$-$C_4$ alkanoyl, or substituted formyl or $C_2$-$C_4$ alkanoyl, where the substituent is $C_3$-$C_6$ cycloalkyl, phenyl, phenyl substituted on adjacent carbon atoms with methylenedioxy, or phenyl substituted with 1, 2 or 3 substituents individually selected from methoxy, ethoxy, bromine, chlorine, fluorine, trifluoromethyl, and $C_1$-$C_4$ alkyl;

and X, Z, n, m, $R^1$, and the R's are as defined for formula I, except $R \neq OCH_3$.

The solvent used in reaction (A) can be any polar solvent which is inert under the reaction conditions. Examples of such solvents are water, lower alkanols, dimethylformamide, dimethylsulfoxide, and dioxane. Preferred is isopropanol. The preferred temperature range is 80°-90° C. The reaction can be run at subatmospheric or superatmospheric pressures, but it is preferred to operate at atmospheric pressure and the reflux temperature of the reaction mass. The reaction involving the formulae IIc and IId type starting material is very fast; refluxing for five minutes at 80°-90° C. is usually sufficient. At lower temperatures, and with the formulae IIa and IIb type starting materials, the reaction is slower, but a reaction time of 24 hours is sufficient in any case.

The compound of formula II will ordinarily be prepared and used in reaction (A) in the form of a salt with a mineral acid such as HCl; the compound of formula I will then be obtained in the form of its salt with the corresponding acid. The free base of formula I can then be obtained simply by treating the salt with a base such as $NH_4OH$ in a solvent such as $CHCl_3$.

A starting material of formula II with $R^2$ other than H can be used in reaction (A) to provide the corresponding compound of formula I. However, it is usually preferred to cyclize a compound of formula II where $R^2$ is H, then acylate to yield an acyl derivative, or acylate and reduce or alkylate to yield an alkyl or substituted alkyl derivative under conventional conditions, to provide the compounds of formula I where $R^1$ is other than H.

The sulfones and sulfoxides of formula I can be made by oxidizing a compound of formula I where $R^1$ is an acyl group with an oxidizing agent which is conventional for such reactions. Suitable oxidizing agents include hydrogen peroxide, organic peracids and sodium metaperiodate for producing sulfoxides, and potassium permanganate for producing sulfones. Sulfones are produced in a neutral solvent such as $CH_2Cl_2$ or $CHCl_3$ at 0° to 25° C. or in glacial acetic acid at 50°-120° C. Sulfoxides are produced in neutral solvents at reflux temperatures in the range of about 50°-75° C.

The sulfones and sulfoxides of formula I wherein $R^1$ is H can be made by hydrolysis of corresponding compounds wherein $R^1$ is acyl.

As stated above, compounds of formula I can be produced directly in the form of mineral acid salts. These can be converted into free bases by treatment with bases, and the free bases can be converted into various pharmaceutically suitable salts by reaction with appropriate acids, in conventional manner. Examples of acids which form pharmaceutically suitable salts with compounds of formula I are: hydrochloric, hydrobromic, sulfuric, sulfamic, phosphoric, nitric, maleic, fumaric, benzoic, ascorbic, citric, pamoic, succinic, methanesulfonic, ethanedisulfonic, acetic, propionic, tartaric, salicylic, gluconic, lactic, malic, mandelic, cinnamic, citraconic, aspartic, stearic, palmitic, itaconic, glycolic, p-aminobenzoic, glutamic, and toluenesulfonic acids.

Compounds of Formula II

Compounds of Formula II can be made by the series of reactions shown in reaction scheme (B):

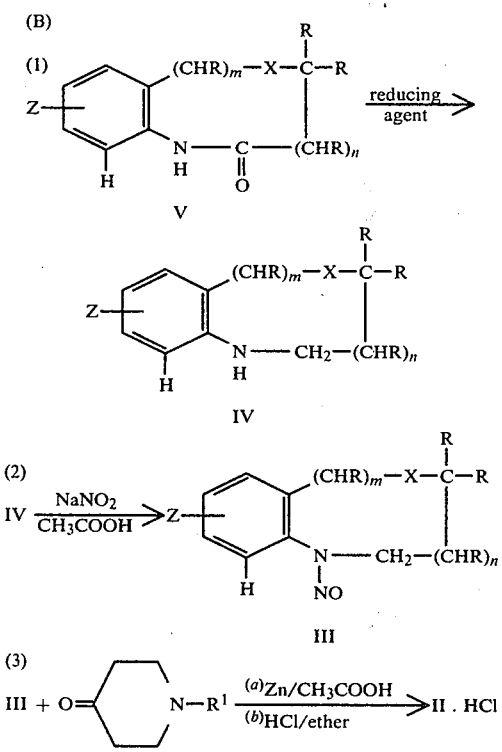

where X, Z, $R^1$, n, m, and the R's have the meanings previously given, except $R \ne OCH_3$.

Many of the compounds of formula V are described in the prior art. The compounds where m is 0 and n is 1 are prepared by reaction of o-aminothiophenol with acrylic acid or an appropriately substituted acrylic acid or by reaction of o-aminophenol with 3-chloropropionyl chloride or a substituted 3-chloropropionyl chloride, followed by cyclization with a base such as KOH or $KOC_2H_5$ in ethanol. The compounds where m and n are both 0 are made by reacting o-aminophenol sodium salt with 2-chloroacetyl chloride or a substituted 2-chloroacetyl chloride or by reacting o-aminothiophenol with an alkyl bromoacetate or an appropriately substituted alkyl bromoacetate. The o-aminophenol sodium salt is obtained by reacting o-aminophenol with sodium hydride in benzene or sodium ethoxide in ethanol. The reaction between o-aminothiophenol and the bromoacetate is carried out in the presence of sodium ethoxide. These reactions for making compounds of formula V can be carried out in ethanol at reflux.

Compounds of formula V wherein m is 1, n is 0 or 1, and X is sulfur can be made by reacting a 2-nitrobenzylchloride with an α-mercaptoacetic acid (for n=0) or a β-mercaptopropionic acid (for n=1), hydrogenating the resulting [(2-nitrobenzyl)thio] acid, then heating the resulting [(2-aminobenzyl)thio] acid to cyclize.

Compounds of formula V wherein m is 1, n is 0 and X is oxygen are made by reducing an aldehyde or ketone of the formula

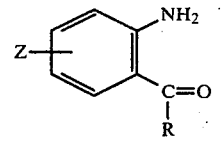

with sodium borohydride to the corresponding benzyl alcohol, reacting the latter with chloroacetyl chloride, then cyclizing with sodium ethoxide. Compounds of formula V wherein m is 1, n is 1 and X is oxygen are made by reacting a 3-chloropropionyl chloride with a 2-aminobenzyl alcohol in a solvent such as anhydrous ether in presence of a base such as triethylamine at a temperature of 0° C. to produce a 2-(chloropropionamido)benzyl alcohol, then cyclizing with sodium ethoxide.

Further information on preparation of compounds of formula V can be found in Mills et al., *J. Chem. Soc.*, 2738 (1927), U.S. Pat. Nos. 3,075,967 and 3,463,773, and French Pat. No. 1,405,271.

Conditions for reactions B(1), (2) and (3) are adequately described in the examples which follow. A solvent such as ethanol is usually used to aid in solubility of the nitroso compound of formula III. After reaction with the piperidone, the hydrazone of formula II is isolated as the free base, and is then preferably converted to a salt by treatment with a solvent such as diethylether saturated with gaseous HCl.

As an alternative to reaction B(3), the nitroso compound of formula III can be reduced to a hydrazine, the hydrazine isolated and then reacted with an appropriate piperidone. These reactions are illustrated by scheme (C):

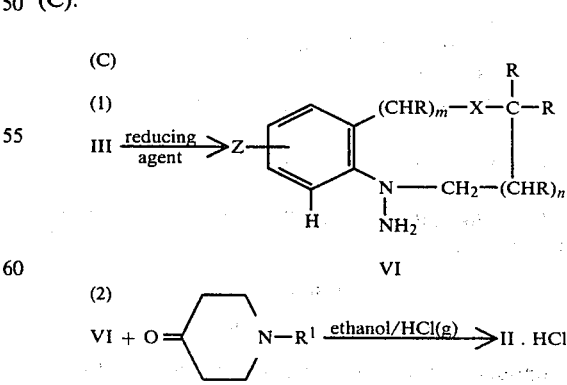

Reaction (C)(1) is carried out in a solvent such as ethanol. Zinc dust and acetic acid can be used as in reaction (B)(3), but other reducing means can also be used. For example, catalytic hydrogenation or reaction with lithium aluminum hydride or sodium dihydrobis(2-methoxyethanolato)aluminate can be used. After reaction (C)(1) is complete, the hydrazine of formula VI is isolated, then dissolved in ethanol saturated with gaseous HCl. Reaction (C)(2) is carried out in this medium at reflux temperature for about ½ to 6 hours.

Compounds of formula I substituted with methoxy on ring A can be made by the following reaction schemes:

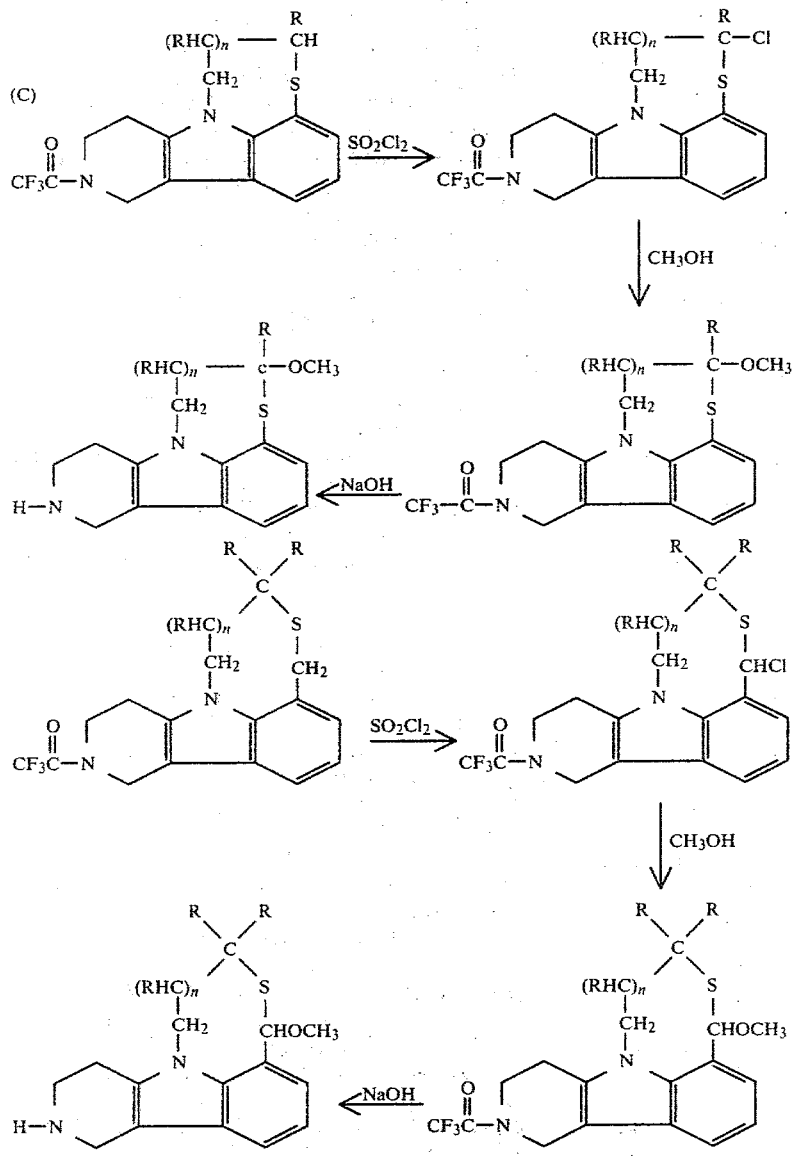

Compounds of formula I which are substituted on ring A can have one, two, or three asymmetric carbon atoms, and thus exist in stereoisomeric forms. This invention includes all of the stereoisomers and mixtures thereof. Example 109 below illustrates the resolution of the racemate into one of its optically active components.

In the following Examples, all temperatures are in degrees centigrade.

EXAMPLE 1

2,3,4,5-tetrahydro-5-nitroso-1,5-benzothiazepine

A solution of 110.4 g of sodium nitrite in 220 ml of water is added dropwise to a well-stirred solution of 181.5 g of 2,3,4,5-tetrahydrobenzothiazepine in 600 ml of glacial acetic acid, cooled in an ice-bath. After the addition is complete the mixture is stirred at room temperature for 30 minutes and then filtered. The crystalline solid is washed with water and air-dried. Recrystallization from hexane yields 2,3,4,5-tetrahydro-5-nitroso-1,5-benzothiazepine as cream colored crystals, m.p. 85°–86°.

EXAMPLES 2–20

The following compounds are prepared by a procedure similar to that described in Example 1:

(2) 2,3,4,5-tetrahydro-2-methyl-5-nitroso-1,5-benzothiazepine, cream colored crystals, m.p. 64°–65°

(3) 2,3,4,5-tetrahydro-3-methyl-5-nitroso-1,5-benzothiazepine, yellow liquid.

(4) 2,3,4,5-tetrahydro-2,2-dimethyl-5-nitroso-1,5-benzothiazepine, cream colored crystals
(5) 2,3,4,5-tetrahydro-5-nitroso-2-phenyl-1,5-benzothiazepine, yellow crystals, m.p. 112°–114°
(6) 2,3,4,5-tetrahydro-5-nitroso-2-(3,4,5-trimethoxyphenyl)-1,5-benzothiazepine, cream colored crystals, m.p. 127°–129° C.
(7) 2-(p-chlorophenyl)-2,3,4,5-tetrahydro-1,5-benzothiazepine, viscous brown liquid
(8) 2,3-dihydro-4-nitroso-4H-1,4-benzothiazine, reddish brown liquid
(9) 1,2,3,5-tetrahydro-1-nitroso-4,1-benzothiazepine, light yellow crystals, m.p. 88°–9°
(10) 1,3,4,6-tetrahydro-1-nitroso-2H-5,1-benzothiazocine, light yellow crystals, m.p. 56°–58°
(11) (±)-2-ethyl-2,3,4,5-tetrahydro-5-nitroso-1,5-benzothiazepine, yellow liquid
(12) (±)-2,3,4,5-tetrahydro-5-nitroso-2-propyl-1,5-benzothiazepine, yellow liquid
(13) (±)-2,3,4,5-tetrahydro-5-nitroso-2-pentyl-1,5-benzothiazepine, yellow liquid
(14) (±)-2,3,4,5-tetrahydro-5-nitroso-2-nonyl-1,5-benzothiazepine, yellow liquid
(15) (±)-2-heptyl-2,3,4,5-tetrahydro-5-nitroso-1,5-benzothiazepine, yellow liquid
(16) (±)-3,4-dihydro-2-methyl-4-nitroso-2H-1,4-benzothiazine, yellow crystals, m.p. 40°–41°
(17) 7-chloro-1,2,3,5-tetrahydro-1-nitroso-4,1-benzothiazepine
(18) 8-chloro-1,3,4,6-tetrahydro-2H-5,1-benzothiazocine
(19) 1,2,3,4-tetrahydro-7-methyl-5-nitroso-1,5-benzothiazepine
(20) 2,3-dihydro-6-methyl-4-nitroso-4H-1,4-benzothiazine

EXAMPLE 21

2,3,8,9,10,11-hexahydro-1H-pyrido[3',4':4,5]pyrrolo[1,2,3-ef][1,5]benzothiazepine hydrochloride Glacial acetic acid (700 ml) is added dropwise to a vigorously stirred mixture of 62 g of 2,3,4,5-tetrahydro-5-nitroso-1,5-benzothiazepine, 49 g of 4-piperidone hydrochloride monohydrate, 400 ml of anhydrous ethanol, and 140 g of zinc dust, cooled in an ice-bath. After the addition is complete, the mixture is stirred at room temperature for 1 hr. and filtered. The residue is washed with a small quantity of ethanol and the combined filtrates heated at 65°–70° C. for 1 hour and then stripped of ethanol and acetic acid under reduced pressure. The residual viscous liquid is dissolved in minimum quantity of water and added with stirring, to excess of well-cooled 25% aqueous sodium hydroxide. The mixture is thoroughly extracted with chloroform and the combined chloroform extracts washed well with water, dried over anhydrous magnesium sulfate and stripped of the solvent under reduced pressure. The residue on trituration with ether and cooling yields 2,3,4,5-tetrahydro-5-[(4-piperidylidene)amino]-1,5-benzothiazepine as cream colored crystals, m.p. 113°–115°. A sample of this hydrazone melts at 115°–117° C. after recrystallization from a mixture of benzene and hexane.

The aforementioned hydrazone is converted into its hydrochloride by dissolving it in anhydrous tetrahydrofuran and adding the solution, with stirring, to an excess of anhydrous ether saturated with gaseous hydrogen chloride. A solution-suspension of 25 g of the hydrochloride thus obtained in 500 ml isopropanol is refluxed for 4 hours, cooled in an ice-bath and filtered. The solid is washed with anhydrous ether and recrystallized from a large quantity of anhydrous ethanol to yield 2,3,8,9,10,11-hexahydro-1H-pyrido[3',4':4,5]pyrrolo[1,2,3-ef][1,5]benzothiazepine hydrochloride, m.p. 293°–295° (dec.), as colorless crystals. The corresponding lactate and acetate, both salts being better than 10% soluble in water, melt at 173°–175° and 129°–130°, respectively.

EXAMPLES 22–59

The following compounds are prepared by a procedure similar to that described in Example 9:
(22) (±)-2,3,8,9,10,11-hexahydro-3-phenyl-1H-pyrido[3',4':4,5]pyrrolo[1,2,3-ef][1,5]benzothiazepine hydrochloride, m.p. 276°–278° (dec.)
(23) (±)-3-(p-chlorophenyl)-2,3,8,9,10,11-hexahydro-1H-pyrido[3',4':4,5]pyrrolo[1,2,3-ef][1,5]benzothiazepine methanesulfonate, m.p. 206°–207° (dec.)
(24) (±)-2,3,8,9,10,11-hexahydro-3-(3,4,5-trimethoxyphenyl)-1H-pyrido[3',4':4,5]pyrrolo[1,2,3-ef][1,5]benzothiazepine hydrochloride, m.p. 284°–285° (dec.)
(25) (±)-2,3,8,9,10,11-hexahydro-2-methyl-1H-pyrido[3',4':4,5]pyrrolo[1,2,3-ef][1,5]benzothiazepine hydrochloride, m.p. 276°–277° (dec.)
(26) (±)-2,3,8,9,10,11-hexahydro-3-methyl-1H-pyrido[3',4':4,5]pyrrolo[1,2,3-ef][1,5]benzothiazepine hydrochloride, m.p. 276°–278° (dec.)
(27) 2,3,8,9,10,11-hexahydro-3,3-dimethyl-1H-pyrido[3',4':4,5]pyrrolo[1,2,3-ef][1,5]benzothiazepine hydrochloride, m.p. 298°–300° (dec.)
(28) 1,2,7,8,9,10-hexahydroyrido[3',4':4,5]pyrrolo[1,2,3-de][1,4]benzothiazine hydrochloride, m.p. 290°–292° (dec.)
(29) 2,3,8,9,10,11-hexahydro-1H-pyrido[3',4':4,5]pyrrolo[1,2,3-ef][1,5]benzothiazepine-9-carboxylic acid ethyl etser, m.p. 168°–170° (dec.)
(30) 2,3,8,9,10,11-hexahydro-9-methyl-1H-pyrido[3',4':4,5]pyrrolo[1,2,3-ef][1,5]benzothiazepine hydrochloride, m.p. 268°–270° (dec.)
(31) 9-(cyclopropylmethyl)-2,3,8,9,10,11-hexahydro-1H-pyrido[3',4':4,5]pyrrolo[1,2,3-ef][1,5]benzothiazepine hydrochloride, m.p. 256°–258° (dec.)
(32) 9-benzyl-2,3,8,9,10,11-hexahydro-1H-pyrido[3',4':4,5]pyrrolo[1,2,3-ef][1,5]benzothiazepine hydrochloride, m.p. 265°–267° (dec.)
(33) 2,3,8,9,10,11-hexahydro-9-phenethyl-1H-pyrido[3',4':4,5]pyrrolo[1,2,3-ef][1,5]benzothiazepine hydrochloride, m.p. 260°–262° (dec.)
(34) (±)-2,3,8,9,10,11-hexahydro-9-phenethyl-3-phenyl-1H-pyrido[3',4':4,5]pyrrolo[1,2,3-ef][1,5]benzothiazepine methanesulfonate, m.p. 193°–195°
(35) 1,2,7,8,9,10-hexahydro-8-phenethylpyrido[3',4':4,5]pyrrolo[1,2,3-de][1,4]benzothiazine hydrochloride, m.p. 265°–267° (dec.)
(36) 9-butyl-2,3,8,9,10,11-hexahydro-1H-pyrido[3',4':4,5]pyrrolo[1,2,3-ef][1,5]benzothiazepine hydrochloride, m.p. 260°–262° (dec.)
(37) 9-cyclopropyl-2,3,8,9,10,11-hexahydro-1H-pyrido[3',4':4,5]pyrrolo[1,2,3-ef][1,5]benzothiazepine hydrochloride, m.p. 248°–250° (dec.)
(38) 1,2,7,8,9,10-hexahydro-8-methylpyrido[3',4':4,5-]pyrrolo[1,2,3-de][1,4]benzothiazepine hydrochloride, m.p. 270°–272° (dec.)
(39) 1,2,8,9,10,11-hexahydro-4H-pyrido[3',4':4,5]pyrrolo[3,2,1-jk][4,1]benzothiazepine hydrochloride, off-white crystals, m.p. 277°–278° (dec.)

(40) 2,3,9,10,11,12-hexahydro-1H,5H-pyrido[3',4':4,5-]pyrrolo[3,2,1-kl][5,1]benzothiazocine hydrochloride, colorless crystals, m.p. 260°-262° (dec.)

(41) (±)-9-cyclopropyl-2,3,8,9,10,11-hexahydro-3-methyl-1H-pyrido[3',4':4,5]pyrrolo[1,2,3-ef][1,5]benzothiazepine hydrochloride, colorless crystals, m.p. 248°-250° (dec.)

(42) (±)-2,3,8,9,10,11-hexahydro-3-propyl-1H-pyrido[3',4':4,5]pyrrolo[1,2,3-ef][1,5]benzothiazepine hydrochloride, colorless, shiny crystals, m.p. 275°-277° (dec.)

(43) 8-cyclopropyl-1,2,7,8,9,10-hexahydropyrido[3',4':4,5]pyrrolo[1,2,3-de][1,4]benzothiazine hydrochloride, colorless crystals, m.p. 238°-240°

(44) (±)-3-ethyl-2,3,8,9,10,11-hexahydro-1H-pyrido[3',4':4,5]pyrrolo[1,2,3-ef][1,5]benzothiazepine hydrochloride, colorless crystals, m.p. 263°-265° (dec.)

(45) (±)-2,3,8,9,10,11-hexahydro-3-nonyl-1H-pyrido[3',4':4,5]pyrrolo[1,2,3-ef][1,5]benzothiazepine hydrochloride, colorless crystals, m.p. 268°-270° (dec.)

(46) (±)-8-cyclopropyl-1,2,7,8,9,10-hexahydro-2-methylpyrido[3',4':4,5]pyrrolo[1,2,3-de][1,4]benzothiazine hydrochloride, colorless crystals, m.p. 268°-270° (dec.)

(47) (±)-2,3,8,9,10,11-hexahydro-3-pentyl-1H-pyrido[3',4':4,5]pyrrolo[1,2,3-ef][1,5]benzothiazepine hydrochloride, colorless crystals, m.p. 273°-275° (dec.)

(48) (±)-9-cyclopropyl-2,3,8,9,10,11-hexahydro-3-pentyl-1H-pyrido[3',4':4,5]pyrrolo[1,2,3-ef][1,5]benzothiazepine hydrochloride, colorless crystals, m.p. 240°-242° (dec.)

(49) (±)-9-(cyclopropylmethyl)-2,3,8,9,10,11-hexahydro-3-methyl-1H-pyrido[3',4':4,5]pyrrolo[1,2,3-ef][1,5]benzothiazepine hydrochloride, colorless crystals, m.p. 248°-249° (dec.)

(50) 8-(cyclopropylmethyl)-1,2,7,8,9,10-hexahydropyrido-[3',4':4,5]pyrrolo[1,2,3-de][1,4]benzothiazine ydrochlorie, off-white crystals, m.p. 255°-256° (dec.)

(51) (±)-3-heptyl-2,3,8,9,10,11-hexahydro-1H-pyrido[3',4':4,5]-pyrrolo[1,2,3-ef][15]benzothiazepine hydrochloride, colorless powder, m.p. 278°-280° (dec.)

(52) (±)-2,3,8,9,10,11-hexahydro-3,9-dimethyl-1H-pyrido[3',4':4,5]pyrrolo[1,2,3-ef][1,5]benzothiazepine hydrochloride, colorless crystals, m.p. 256°-257° (dec.)

(53) (3S)-9-benzyl-2,3,8,9,10,11-hexahydro-3-methyl-1H-pyrido[3',4':4,5]pyrrolo[1,2,3-ef][1,5]benzothiazepine hydrochloride, colorless crystals, m.p. 255°-257°

(54) 6-chloro-1,2,8,9,10,11-hexahydro-4H-pyrido[3',4':4,5]pyrrolo[3,2,1-jk][4,1]benzothiazepine hydrochloride

(55) 6-chloro-9-cyclopropyl-1,2,8,9,10,11-hexahydro-4H-pyrido[3',4':4,5]pyrrolo[3,2,1-jk][4,1]benzothiazepine hydrochloride

(56) 7-chloro-2,3,9,10,11,12-hexahydro-1H,5H-pyrido[3',4':4,5]pyrrolo[3,2,1-kl][5,1]benzothiazocine hydrochloride

(57) 7-chloro-2,3,9,10,11,12-hexahydro-10-methyl-1H,5H-pyrido[3',4':4,5]pyrrolo[3,2,1-kl][5,1]benzothiazocine hydrochloride

(58) 2,3,8,9,10,11-hexahydro-6-methyl-1H-pyrido[3',4':4,5]pyrrolo[1,2,3-ef][1,5]benzothiazepine hydrochloride

(59) 8-cyclopropyl-1,2,7,8,9,10-hexahydropyrido[3',4':4,5]pyrrolo[1,2,3-de][1,4]benzothiazine hydrochloride

EXAMPLE 60

9-allyl-2,3,8,9,10,11-hexahydro-1H-pyrido[3',4':4,5]pyrrolo[1,2,3-ef][1,5]benzothiazepine hydrochloride Allyl bromide (2.4 g) is added, in one lot, to a stirred mixture of 2,3,8,9,10,11-hexahydro-1H-pyrido[3',4':4,5-]pyrrolo[1,2,3-ef][1,5]benzothiazepine (4.9 g), absolute ethanol (50 ml) and powdered anhydrous sodium carbonate (5 g) and the mixture refluxed for 2 hours, stirring being continued. It is then cooled and poured into excess of ice and water and the sticky semi-solid that separates is extracted with chloroform and the chloroform extract is washed with water, dried over anhydrous magnesium sulfate and stripped of the solvent under reduced pressure. The residue is dissolved in requisite quantity of anhydrous ether and added to excess of anhydrous ether saturated with gaseous hydrogen chloride. The solid that separates is filtered, washed with anhydrous ether and recrystallized from isopropyl alcohol and anhydrous ether to yield 9-allyl-2,3,8,9,10,11-hexahydro-1H-pyrido[3',4':4,5]pyrrolo[1,2,3-ef][1,5]benzothiazepine hydrochloride, m.p. 235°-236° (dec).

EXAMPLE 61

2,3,8,9,10,11-hexahydro-9-(trifluoroacetyl)-1H-pyrido[3',4':4,5]pyrrolo[1,2,3-ef][1,5]benzothiazepine Trifluoroacetic anhydride (19.7 g) is added in one lot, to a well-cooled, stirred solution of 2,3,8,9,10,11-hexahydro-1H-pyrido[3',4':4,5]pyrrolo[1,2,3-ef][1,5]benzothiaazepine (15.1 g) in anhydrous pyridine (50 ml) and the resulting mixture is stirred at room temperature for 30 minutes and then poured into excess of ice and water containing 75 ml of concentrated hydrochloric acid. The solid that separates is filtered, washed with water, air-dried and recrystallized from tetrahydrofuran-pentane to yield 2,3,8,9,10,11-hexahydro-9-(trifluoroacetyl)-1H-pyrido[3',4':4,5]pyrrolo[1,2,3-ef][1,5]benzothiazepine, m.p. 140°-142°.

EXAMPLE 62

2,3,8,9,10,11-hexahydro-9-(3,4,5-trimethoxybenzyl)-1H-pyrido[3',4':4,5]pyrrolo[1,2,3-ef][1,5]benzothiazepine A solution of 2.3 g of 3,4,5-trimethoxybenzoyl chloride in 25 ml of CHCl₃ is added, dropwise, to a vigorously stirred mixture of a solution of 2.3 g of 2,3,8,9,10,11-hexahydro-1H-pyrido[3',4':4,5]pyrrolo[1,2,3ef][1,5]benzothiazepine in 50 ml of chloroform and 50 ml of a saturated solution of sodium carbonate in water. After the addition is complete the mixture is stirred for an additional 15 minutes and the chloroform layer separated, washed successively with water, 2 N hydrochloric acid and water, dried over anhydrous magnesium sulfate and stripped of the solvent. The residual viscous liquid is triturated with ether and the solid thus obtained is filtered and recrystallized from tetrahydrofuran and hexane to yield 2,3,8,9,10,11-hexahydro-9-(3,4,5-trimethoxybenzoyl)-1H-pyrido[3',4':4,5]pyrrolo[1,2,3-ef][1,5]benzothiazepine,

EXAMPLE 63

9-[2-(3,4-dimethoxyphenyl)acetyl]-2,3,8,9,10,11-hexahydro-1H-pyrido[3',4':4,5]pyrrolo[1,2,3-ef][1,5]benzothiazepine A solution of 8 g of dicyclohexylcarbodiimide in 50 ml of chloroform is added, in one lot, to a stirred solution of 9.2 of 2,3,8,9,10,11-hexahydro-1H-pyrido[3',4':4,5]pyrrolo[1,2,3-ef][1,5]benzothiazepine and 7.6 g of (3,4-dimethoxyphenyl)acetic acid in 250 ml of chloroform. The mixture is then stirred for 1 hour and filtered and the filtrate stripped of the solvent under reduced pressure. The residue viscous liquid is triturated with ethanol and the solid thus obtained is filtered and recrystallized from ethanol to yield 9-[2-(3,4-dimethoxyphenyl)acetyl]-2,3,8,9,10,11-hexahydro-1H-pyrido[3',4':4,5]pyrrolo[1,2,3-ef][1,5]benzothiazepine, m.p. 232°–233°.

EXAMPLE 64

9-(3,4-dimethoxyphenethyl)-2,3,8,9,10,11-hexahydro-1H-pyrido[3',4':4,5]pyrrolo[1,2,3-ef][1,5]benzothiazepine hydrochloride Ten grams of a 75% benzene solution of sodium dihydrobis(2-methoxyethanolato)aluminate is added dropwise to a stirred solution-suspension of 4.1 g of 9-[2-(3,4-dimethoxyphenyl)acetyl]-2,3,8,9,10,11-hexahydro-1H-pyrido[3',4':4,5]pyrrolo[1,2,3-ef][1,5]benzothiazepine in 100 ml of anhydrous benzene. After the addition is complete the mixture is stirred and refluxed for 2 hours, cooled in an ice-bath and treated with 20 ml of 20% aqueous sodium hydroxide added dropwise initially and rapidly subsequently. The mixture is then diluted with 200 ml of water, the benzene layer separated, and the aqueous layer is extracted thrice with chloroform. The benzene and chloroform extracts are washed with water, combined, dried over anhydrous magnesium sulfate and stripped of the solvent under reduced pressure. The residual viscous liquid is dissolved in requisite quantity of anhydrous tetrahydrofuran and added to an excess of anhydrous ether saturated with gaseous hydrogen chloride. The solid thus obtained is filtered, washed well with anhydrous ether and recrystallized from ethanol, to yield 9-(3,4-dimethoxyphenethyl)-2,3,8,9,10,11-hexahydro-1H-pyrido[3',4':4,5]pyrrolo[1,2,3-ef][1,5]benzothiazepine hydrochloride, m.p. 253°–255° (dec.).

EXAMPLE 65

2,3,8,9,10,11-hexahydro-1H-pyrido[3',4':4,5]pyrrolo[1,2,3-ef][1,5]benzothiazepine methanesulfonate A solution of 5 g of 2,3,8,9,10,11-hexahydro-1H-pyrido[3',4':4,5]pyrrolo[1,2,3-ef][1,5]benzothiazepine in 50 ml of anhydrous tetrahydrofuran is added in one lot, with agitation, to a solution of 2.5 g of methanesulfonic acid in 50 ml of anhydrous tetrahydrofuran. Immediate precipitation of the salt occurs and the mixture is cooled, filtered, and the solid washed with anhydrous tetrahydrofuran followed by anhydrous ether. It is recrystallized from a mixture of isopropanol and ethanol to yield 2,3,8,9,10,11-hexahydro-1H-pyrido[3',4':4,5-]pyrrolo[1,2,3-ef][1,5]benzothiazepine methanesulfonate, m.p. 225°–226°(dec.).

EXAMPLE 66

2,3,8,9,10,11-hexahydro-1H-pyrido[3',4':4,5]pyrrolo[1,2,3-ef][1,5]benzothiazepine 4-oxide methanesulfonate A solution of m-chloroperbenzoic acid (3.2 g of approximately 85% pure material) in 100 ml of $CH_2Cl_2$ is added in one lot to a stirred solution of 2,3,8,9,10,11-hexahydro-9-(trifluoroacetyl)-1H-pyrido[3',4':4,5]pyrrolo[1,2,3-ef][1,5]benzothiazepine (5.1 g) in 150 ml of $CH_2Cl_2$ cooled to −20°. The mixture is stirred at −20° for 15 minutes and then extracted with 100 ml of aqueous sodium bicarbonate (saturated solution). The $CH_2Cl_2$ is separated, washed with water, dried over anhydrous magnesium sulfate and stripped of the solvent in vacuo. The residual viscous liquid is triturated with anhydrous ether and the mixture is evaporated to remove the ether. The residue is taken up in 50 ml of ethanol, treated with 8 ml of 10% NaOH, refluxed for 1 hour and cooled. Most of the ethanol from the mixture is removed under reduced pressure and the residue diluted with 200 ml of water and extracted twice with chloroform. The combined chloroform layers are washed thoroughly with water, dried over anhydrous magnesium sulfate and stripped of the solvent under reduced pressure. The residual heavy viscous liquid is dissolved in 50 ml of anhydrous THF and added to a solution of 2.8 g of $CH_3SO_3H$ in anhydrous THF with swirling. The solid that separates is filtered, washed with THF and then with ether and recrystallized from a mixture of isopropanol-ethanol-anhydrous ether, m.p. 241°–242° (dec.).

EXAMPLE 67

(±)-3-chloro-2,3,8,9,10,11-hexahydro-9-(trifluoroacetyl)-1H-[3',4':4,5]pyrrolo[1,2,3-ef][1,5]benzothiazepine A solution of sulfuryl chloride (3.9 g) in chloroform (10 ml) is added dropwise to a stirred solution of 2,3,8,9,10,11-hexahydro-9-(trifluoroacetyl)-1H-pyrido[3',4':4,5]pyrrolo[1,2,3-ef][1,5]benzothiazepine (10.2 g) in anhydrous benzene (240 ml). After the addition is complete, the mixture is stirred at room temperature for 30 minutes and stripped of the solvents under reduced pressure and the residue recrystallized from a mixture of tetrahydrofuran and pentane to yield (±)-3-chloro-2,3,8,9,10,11-hexahydro-9-(trifluoroacetyl)-1H-pyrido[3',4':4,5]pyrrolo[1,2,3-ef][1,5]benzothiazepine, m.p. 133°–134°.

EXAMPLES 68–80

By substituting the proper starting material in Example 67, the following compounds can be prepared similarly:

(68) (±)-3-chloro-2,3,8,9,10,11-hexahydro-3-methyl-9-(trifluoroacetyl)-1H-pyrido[3',4':4,5]pyrrolo[1,2,3-ef][1,5]benzothiazepine

(69) (±)-3-chloro-2,3,8,9,10,11-hexahydro-2-methyl-9-(trifluoroacetyl)-1H-pyrido[3',4':4,5]pyrrolo[1,2,3-ef][1,5]benzothiazepine

(70) (±)-3-chloro-2,3,8,9,10,11-hexahydro-3-propyl-9-(trifluoroacetyl)-1H-pyrido[3',4':4,5]pyrrolo[1,2,3-ef][1,5]benzothiazepine

(71) (±)-3-chloro-2,3,8,9,10,11-hexahydro-3-pentyl-9-(trifluoroacetyl)-1H-pyrido[3',4':4,5]pyrrolo[1,2,3-ef][1,5]benzothiazepine

--- m.p. 183°–185°. Reduction by the method of Example 64 yields the title compound.

(72) (±)-3-chloro-2,3,8,9,10,11-hexahydro-3-nonyl-9-(trifluoroacetyl)-1H-pyrido[3',4':4,5]pyrrolo[1,2,3-ef][1,5]benzothiazepine

(73) (±)-3-chloro-2,3,8,9,10,11-hexahydro-3-phenyl-9-(trifluoroacetyl)-1H-pyrido[3',4':4,5]pyrrolo[1,2,3-ef][1,5]benzothiazepine

(74) (±)-3-chloro-3-ethyl-2,3,8,9,10,11-hexahydro-9-(trifluoroacetyl)-1H-pyrido[3',4':4,5]pyrrolo[1,2,3-ef][1,5]benzothiazepine

(75) (±)-3-chloro-3-heptyl-2,3,8,9,10,11-hexahydro-9-(trifluoroacetyl)-1H-pyrido[3',4':4,5]pyrrolo[1,2,3-ef][1,5]benzothiazepine

(76) (±)-3-chloro-3-(p-chlorophenyl)-2,3,8,9,10,11-hexahydro-9-(trifluoroacetyl)-1H-pyrido[3',4':4,5-]pyrrolo[1,2,3-ef][1,5]benzothiazepine

(77) (±)-3-chloro-3-(3,4-dimethoxyphenyl)-2,3,8,9,10,11-hexahydro-9-(trifluoroacetyl)-1H-pyrido[3',4':4,5]pyrrolo[1,2,3-ef][1,5]benzothiazepine

(78) (±)-3-chloro-3-cyclohexyl-2,3,8,9,10,11-hexahydro-9-(trifluoroacetyl)-1H-pyrido[3',4':4,5]pyrrolo[1,2,3-ef][1,5]benzothiazepine

(79) (±)-2-chloro-1,2,7,8,9,10-hexahydro-2-methyl-8-(trifluoroacetyl)pyrido[3',4':4,5]pyrrolo[1,2,3-de][1,4]benzothiazine

(80) (±)-2-chloro-1,2,7,8,9,10-hexahydro-8-(trifluoroacetyl)pyrido[3',4':4,5]pyrrolo[1,2,3-de][1,4]benzothiazine

EXAMPLE 81

(±)-2,3,8,9,10,11-hexahydro-3-methoxy-9-(trifluoroacetyl)-1H-pyrido[3',4':4,5]pyrrolo[1,2,3-ef][1,5]benzothiazepine A mixture of (±)-3-chloro-2,3,8,9,10,11-hexahydro-9-(trifluoroacetyl)-1H-pyrido[3',4':4,5]pyrrolo[1,2,3-ef][1,5]benzothiazepine (5.5 g) and methanol (75 ml) is refluxed on a steam bath for 30 minutes and then stripped of the solvent under pressure. The residue is recrystallized from isopropanol to yield (±)-2,3,8,9,10,11-hexahydro-3-methoxy-9-(trifluoroacetyl)-1H-pyrido[3',4':4,5]pyrrolo[1,2,3-ef][1,5]benzothiazepine, 155°-156°.

EXAMPLES 82-94

By substituting the compounds of Examples 68-80 as starting materials in the procedure of Example 81, the following compounds can be prepared:

(82) (±)-2,3,8,9,10,11-hexahydro-3-methoxy-3-methyl-9-(trifluoroacetyl)-1H-pyrido[3',4':4,5]pyrrolo[1,2,3-ef][1,5]benzothiazepine

(83) (±)-2,3,8,9,10,11-hexahydro-3-methoxy-2-methyl-9-(trifluoroacetyl)-1H-pyrido[3',4':4,5]pyrrolo[1,2,3-ef][1,5]benzothiazepine

(84) (±)-2,3,8,9,10,11-hexahydro-3-methoxy-3-propyl-9-(trifluoroacetyl)-1H-pyrido[3',4':4,5]pyrrolo[1,2,3-ef][1,5]benzothiazepine

(85) (±)-2,3,8,9,10,11-hexahydro-3-methoxy-3-pentyl-9-(trifluoroacetyl)-1H-pyrido[3',4':4,5]pyrrolo[1,2,3-ef][1,5]benzothiazepine

(86) (±)-2,3,8,9,10,11-hexahydro-3-methoxy-3-nonyl-9-(trifluoroacetyl)-1H-pyrido[3',4':4,5]pyrrolo[1,2,3-ef][1,5]benzothiazepine

(87) (±)-2,3,8,9,10,11-hexahydro-3-methoxy-3-phenyl-9-(trifluoroacetyl)-1H-pyrido[3',4':4,5]pyrrolo[1,2,3-ef][1,5]benzothiazepine

(88) (±)-3-ethyl-2,3,8,9,10,11-hexahydro-3-methoxy-9-(trifluoroacetyl)-1H-pyrido[3',4':4,5]pyrrolo[1,2,3-ef][1,5]benzothiazepine

(89) (±)-3-heptyl-2,3,8,9,10,11-hexahydro-3-methoxy-9-(trifluoroacetyl)-1H-pyrido[3',4':4,5]pyrrolo[1,2,3-ef][1,5]benzothiazepine

(90) (±)-3-(p-chlorophenyl)-2,3,8,9,10,11-hexahydro-3-methoxy-9-(trifluoroacetyl)-1H-pyrido[3',4':4,5]pyrrolo[1,2,3-ef][1,5]benzothiazepine

(91) (±)-3,4-dimethoxyphenyl-2,3,8,9,10,11-hexahydro-3-methoxy-9-(trifluoroacetyl)-1H-pyrido[3',4':4,5]pyrrolo[1,2,3-ef][1,5]benzothiazepine

(92) (±)-3-cyclohexyl-2,3,8,9,10,11-hexahydro-3-methoxy-9-(trifluoroacetyl)-1H-pyrido[3',4':4,5]pyrrolo[1,2,3-ef][1,5]benzothiazepine

(93) (±)-1,2,7,8,9,10-hexahydro-2-methoxy-2-methyl-8-(trifluoroacetyl)pyrido[3',4':4,5]pyrrolo[1,2,3-de][1,4]benzothiazine

(94) (+)-1,2,7,8,9,10-hexahydro-2-methoxy-8-(trifluoroacetyl)pyrido[3',4':4,5]pyrrolo[1,2,3-de][1,4]benzothiazine

EXAMPLE 95

(±)-2,3,8,9,10,11-hexahydro-3-methoxy-1H-pyrido[3',4':4,5]pyrrolo[1,2,3-ef][1,5]benzothiazepine maleate (1:1)

A mixture of (±)-2,3,8,9,10,11-hexahydro-3-methoxy-9-(trifluoroacetyl)-1H-pyrido[3',4':4,5]pyrrolo[1,2,3-ef][1,5]benzothiazepine (4.8 g), ethanol (50 ml) and 5% aqueous sodium hydroxide (10 ml) is refluxed for 1 hour and then stripped of most of the ethanol under reduced pressure. The residue is treated with water and extracted with ether. The ether extract is washed with water, dried over anhydrous magnesium sulfate and stripped of the solvent under reduced pressure. The residual viscous liquid is dissolved in a minimum quantity of anhydrous ether and added to a solution of maleic acid (1.6 g) in requisite quantity of anhydrous ether. The solid that separates is filtered, washed with ether and recrystallized from isopropanol to yield (±)-2,3,8,9,10,11-hexahydro-3-methoxy-1H-pyrido[3',4':4,5]pyrrolo[1,2,3-ef][1,5]benzothiazepine maleate, m. p. 165°-166°.

EXAMPLES 96-108

By substituting the compounds of Examples 82-94 as starting materials in the procedure of Example 95, then converting the maleate salts to the free bases, the following compounds can be prepared:

(96) (±)-2,3,8,9,10,11-hexahydro-3-methoxy-3-methyl-1H-pyrido[3',4':4,5]pyrrolo[1,2,3-ef][1,5]benzothiazepine

(97) (±)-2,3,8,9,10,11-hexahydro-3-methoxy-2-methyl-1H-pyrido[3',4':4,5]pyrrolo[1,2,3-ef][1,5]benzothiazepine

(98) (±)-2,3,8,9,10,11-hexahydro-3-methoxy-3-propyl-1H-pyrido[3',4':4,5]pyrrolo[1,2,3-ef][1,5]benzothiazepine

(99) (±)-2,3,8,9,10,11-hexahydro-3-methoxy-3-pentyl-1H-pyrido[3',4':4,5]pyrrolo[1,2,3-ef][1,5]benzothiazepine (100) (±)-2,3,8,9,10,11-hexahydro-3-methoxy-3-nonyl-1H-pyrido[3',4':4,5]pyrrolo[1,2,3ef][1,5]benzothiazepine (101) (±)-2,3,8,9,10,11-hexahydro-3-methoxy-3-phenyl-1H-pyrido[3',4':4,5]pyrrolo[1,2,3-ef][1,5]benzothiazepine (102) (±)-3-ethyl-2,3,8,9,10,11-hexahydro-3-methoxy-1H-pyrido[3',4':4,5]pyrrolo[1,2,3-ef][1,5]benzothiazepine (103) (±)-3-heptyl-2,3,8,9,10,11-hexahydro-3-methoxy-1H-pyrido[3',4':4,5]pyrrolo[1,2,3-ef][1,5]benzothiazepine (104) (±)-3-(p-chlorophenyl)-2,3,8,9,10,11-hexahydro-3-methoxy-1H-pyrido[3',4':4,5]pyrrolo[1,2,3-ef][1,5]benzothiazepine (105) (±)-3-(3,4-dimethoxyphenyl)-2,3,8,9,10,11-hexahydro-3-methoxy-1H-pyrido[3',4':4,5]pyrrolo[1,2,3-ef][1,5]benzothiazepine (106) (±)-3-cyclohexyl-2,3,8,9,10,11-hexahydro-3-methoxy-1H-pyrido[3',4':4,5]pyrrolo[1,2,3-ef][1,5]benzothiazepine (107) (±)-1,2,7,8,9,10-hexahydro-2-methoxy-2-methyl-pyrido[3',4':4,5]pyrrolo[1,2,3-de][1,4]benzothiazine (108) (+)-1,2,7,8,9,10-hexahydro-2-methoxypyrido[3',4':4,5]pyrrolo[1,2,3-de][1,4]benzothiazine

EXAMPLE 109

(±)-2,3,8,9,10,11-hexahydro-3-methyl-1H-pyrido[3',4':4,5]pyrrolo[1,2,3-ef][1,5]benzothiazepine hydrochloride (±)-2,3,8,9,10,11-Hexahydro-3-methyl-1H-pyrido[3',4':4,5]pyrrolo[1,2,3-ef][1,5]benzothiazepine hydrochloride is converted to its base by treatment with ammonium hydroxide, extraction with CHCl$_3$, evaporation of the solvent and recrystallization of the residue from hexane, m.p. 110°-112°. A solution of this base (8.6 g) in anhydrous tetrahydrofuran (30 ml) is added to a solution of (−)-2,3:3,6-di-O-isopropylidene-2-keto-L-gulonic acid hydrate ([α]$_D^{25}$ = −21.3° (2% in methanol) (9.8 g) in anhydrous tetrahydrofuran (100 ml), with agitation. After 15 minutes the mixture is stripped of the solvent under reduced pressure and the viscous, syrupy residue is triturated with isopropanol whereupon it solidifies. The solid is filtered and recrystallized from isopropanol until successive specific rotations are close. (After four recrystallizations [α]$_D^{27}$ = −63.81), m.p. 125°-127° (foaming). The free base is liberated from the salt with ammonium hydroxide, isolated by extraction with CHCl$_3$ and converted to its hydrochloride by dissolution in anhydrous tetrahydrofuran and addition to excess of anhydrous ether saturated with gaseous hydrogen chloride. Recrystallization from methanol yields (+)-2,3,8,9,10,11-hexahydro-3-methyl-1H-pyrido[3',4':4,5]pyrrolo[1,2,3-ef][1,5]benzothiazepine hydrochloride, m.p. 276°-278° (dec.), [α]$_D^{27}$ = +8.30 (c 2% in methanol).

EXAMPLE 110

1,2,8,9,10,11-hexahydro-4H-pyrido[3',4':4,5]pyrrolo[3,2,1-jk][4,1]benzoxazepine hydrochloride 1,2,3,5-Tetrahydro-4,1-benzoxazepine, prepared according to E. Testa and L. Fontanella, Fr. Pat. No. 1,405,271, is converted to the corresponding 5-nitroso derivative as described in Example 1 obtained as yellow crystals, m.p. 62°-64° C. The latter, 8.3 g, is dissolved in 130 ml of methanol. To the resulting solution, cooled to 10°-15° C. there is added 20 g of Zn dust in small portions along with 25 ml of acetic acid, added dropwise. After the addition is complete, the mixture is stirred at room temperature for 3 hours and then filtered. The filtrate is stripped of the solvent under reduced pressure and the oily residue is treated with 5 N HCl to yield 1-amino-1,2,3,5-tetrahydro-4,1-benzoxazepine hydrochloride, which is filtered and washed on the filter with ether, m.p. 229°-230°. The aforementioned hydrazine hydrochloride (3 g.) is reacted with 2.6 g of 4-piperidone hydrochloride in 30 ml of ethanol saturated with gaseous HCl by heating to reflux for 2 hours. The HCl salt of 1,2,8,9,10,11-hexahydro-4H-pyrido[3',4':4,5]pyrrolo[3,2,1-jk][4,1]benzoxazepine separates out in the course of the reaction. The product was cooled, filtered, and recrystallized from ethanol. Melting point of the resulting product was 296°-297°.

EXAMPLE 111

1,2,8,9,10,11-hexahydro-9-methyl-4H-pyrido[3',4':4,5]pyrrolo[3,2,1-jk][4,1]benzoxazepine hydrochloride By a procedure similar to that described in Example 110, 1-amino-1,2,3,5-tetrahydro-4,1-benzoxazepine hydrochloride is reacted with 1-methyl-4-piperidone to yield the title compound, m.p. 286°-288°.

EXAMPLE 112

(±)-1,2,8,9,10,11-hexahydro-4-phenyl-4H-pyrido[3',4':4,5]pyrrolo[3,2,1-jk][4,1]benzoxazepine hydrochloride 1-Amino-1,2,3,5-tetrahydro-5-phenyl-4,1-benzoxazepine [Testa and Fontanella, Il Farmaco, 18, 815 (1963)] is reacted with 4-piperidone hydrochloride as described in Example 110 to yield the title compound, m.p. 297°-299°.

EXAMPLE 113

6-chloro-1,2,8,9,10,11-hexahydro-4H-pyrido[3',4':4,5]pyrrolo[3,2,1-jk][4,1]benzoxazepine hydrochloride By the procedure described in Example 1, the appropriate benzoxazepine is converted to 7-chloro-1,2,3,5-tetrahydro-1-nitroso-4,1-benzoxazepine, m.p. 54°-56°. The latter is reduced to the corresponding 1-amino derivative hydrochloride, which is reacted with 4-piperidone hydrochloride to yield the title compound, m.p. 304°-305°.

EXAMPLE 114

1,2,8,9,10,11-hexahydro-6-methyl-4H-pyrido[3',4':4,5]pyrrolo[3,2,1-jk][4,1]benzoxazepine hydrochloride In a manner analogous to the preparation of 1,2,3,5-tetrahydro-4,1-benzoxazepine (E. Testa and L. Fontanella, Fr. Pat. No. 1,405,271), 5-methylanthranilic acid is converted to 1,2,3,5-tetrahydro-7-methyl-4,1-benzoxazepine, m.p. 102°, which, by a procedure similar to that described in Example 110, is converted to the title compound, m.p. 320° (dec).

EXAMPLE 115

(±)-1,2,8,9,10,11-hexahydro-4-methyl-4H-pyrido[3',4':4,5]pyrrolo[3,2,1-jk][4,1]benzoxazepine hydrochloride According to the procedure described in Example 1, the appropriate benzoxazepine is converted to 1-amino-1,2,3,5-tetrahydro-5-methyl-4,1-benzoxazepine hydrochloride, m.p. 198°-200°, which is reacted with 4-piperidone hydrochloride to yield the title compound, m.p. 285°-286° (dec.).

EXAMPLE 116

2,3,9,10,11,12-hexahydro-1H,5H-pyrido[3',4':4,5]pyrrolo[3,2,1-kl][5,1]benzoxazocine hydrochloride A solution of 2.54 g of β-chloropropionyl chloride in 30 ml of anhydrous ether is added slowly to a stirred solution of 2.13 g of 2-aminobenzyl alcohol in 100 ml of anhydrous ether and 1.8 ml of triethylamine previously cooled to 0° C. After the addition is complete, stirring is continued for another hour, keeping the reaction mixture at 0° C. Water (30 ml.) is then added, and the reaction mixture is acidified with hydrochloric acid. The ether layer is separated, washed with an aqueous saturated solution of sodium chloride, dried with sodium sulfate, filtered and evaporated to dryness. The resulting 2-(2-chloropropionamido)benzyl alcohol is converted, in a manner similar to that described for the preparation of 1,2,3,5-tetrahydro-4,1-benzoxazepine (E. Testa and L. Fontanella, Fr. Pat. No. 1,405,271) to 1,3,4,6-tetrahydro-2H-5,1-benzoxazocine. The latter, by a procedure similar to that described in Example 110 is converted to the title compound.

EXAMPLE 117

1,2,7,8,9,10-hexahydropyrido[3',4':4,5]pyrrolo[1,2,3-de][1,4]benzoxazine hydrochloride Chloroacetyl chloride (104 g) is added slowly to a stirred mixture of o-aminophenol (96 g), sodium bicarbonate (100 g) and chloroform (1400 ml). After the addition is complete the reaction mixture is stirred at room temperature for 2 hours. The resulting chloroacetamide derivative, which separates in the course of the reaction, is filtered and added with stirring to 1 liter of NaOH, producing 2H-1,4-benzoxazin-3(4H)-one, which is filtered and washed with $H_2O$, m.p. 169°–170°. The latter (30 g) is added portionwise to a suspension of 26 g of $LiAlH_4$ in 1500 ml of anhydrous ether, keeping the temperature at 10° during the addition. After the addition is complete the reaction mixture is heated to reflux for 2 hours. It is then cooled, decomposed with water and filtered. The organic layer is separated and dried over anhydrous sodium sulfate; the solvent is removed in the rotary evaporator and the oily product obtained distilled to yield 3,4-dihydro-2H-1,4-benzoxazine ($b_{760}$ 265°–267°). In a like manner as in Example 1, the latter benzoxazine is converted to the corresponding 4-nitroso derivative, which is worked up as described in Example 110 to give 4-amino-3,4-dihydro-2H-1,4-benzoxazine hydrochloride [m.p. 160° (dec.)] and finally the title compound m.p. 255° (dec.).

EXAMPLE 118

1,2,7,8,9,10-hexahydro-8-methylpyrido[3',4':4,5]pyrrolo[1,2,3-de][1,4]benzoxazine hydrochloride By a procedure similar to Example 110, 4-amino-3,4-dihydro-2H-1,4-benzoxazine hydrochloride is reacted with 1-methyl-4-piperidone to yield the title compound, m.p. 245°–246°.

EXAMPLE 119

8-cyclopropyl-1,2,7,8,9,10-hexahydropyrido[3',4':4,5]pyrrolo[1,2,3-de][1,4]benzoxazine hydrochloride 4-Amino-3,4-dihydro-2H-1,4-benzoxazine hydrochloride is reacted with 1-cyclopropyl-4-piperidone according to the procedure of Example 110 to yield the title compound, m.p. 232°–233°.

EXAMPLE 120

1,2,7,8,9,10-hexahydro-5-methylpyrido[3',4':4,5]pyrrolo[1,2,3-de][1,4]benzoxazine hydrochloride Starting with 2-amino-5-methylphenol and following the procedure of Example 117, 4-amino-3,4-dihydro-7-methyl-2H-1,4benzoxazine hydrochloride is obtained, m.p. 148° (dec.), which is reacted with 4-piperidone hydrochloride to yield the title compound, m.p. 300° (dec.).

EXAMPLE 121

1,2,7,8,9,10-hexahydro-5,8-dimethylpyrido[3',4':4,5-]pyrrolo[1,2,3-de][1,4]benzoxazine hydrochloride 4-Amino-3,4-dihydro-7-methyl-2H-1,4-benzoxazine hydrochloride is reacted with 1-methyl-4-piperidone according to the procedure of Example 110 to yield the title compound, m.p. 248°–249°.

EXAMPLE 122

1,2,7,8,9,10-hexahydro-6-methylpyrido[3',4':4,5]pyrrolo[1,2,3-de][1,4]benzoxazine hydrochloride Starting with 2-amino-4-methylphenol and following the procedure of Example 117, 4-amino-3,4-dihydro-6-methyl-2H-1,4-benzoxazine hydrochloride is obtained, m.p. 153°–155° (dec.), which is reacted with 4-piperidone hydrochloride to yield the title compound, m.p. 328°–329° (dec.).

EXAMPLE 123

(±)-1,2,7,8,9,10-hexahydro-2-phenylpyrido[3',4':4,5-]pyrrolo[1,2,3-de][1,4]benzoxazine hydrochloride By a procedure similar to that described for the synthesis of 3,4-dihydro-2H-1,4-benzoxazine (Example 142), o-aminophenol and 2-chlorophenylacetyl chloride produces 3,4-dihydro-2-phenyl-2H-1,4-benzoxazine, m.p. 113°–116° which, according to the reaction scheme of Example 110 is converted to the title compound, m.p. 311°–313°.

EXAMPLE 124

(±)-1,2,7,8,9,10-hexahydro-8-methyl-2-phenyl-pyrido[3',4':4,5]pyrrolo1,2,3-de][1,4]benzoxazine hydrochloride By the reaction scheme described in Example 110, 3,4-dihydro-2-phenyl-2H-1,4-benzoxazine is converted to the corresponding 4-amino derivative which is reacted with 1-methyl-4-piperidone to give the title compound, m.p. 274°–276°.

EXAMPLE 125

2,3,8,9,10,11-hexahydro-1H-pyrido[3',4':4,5]pyrrolo[1,2,3-ef][1,5]benzoxazepine hydrochloride By a procedure similar to that described in Example 1 2,3,4,5-tetrahydro-1,5-benzoxazepine [G. S. Sidhu et al. Indian J. Chem. 2, 211 (1964)] is converted to the corresponding 5-nitroso derivative. The latter, which separates as a heavy oil, is converted, according to the reaction scheme described in Example 110, to 5-amino-2,3,4,5-tetrahydro-1,5-benzoxazepine hydrochloride, m.p. 192°–194° which is reacted with 4-piperidone to yield the title compound, m.p. 283°–285° (dec.).

EXAMPLES 126–129

By the procedure of Example 125, the following compounds can be prepared, starting from 2,3,4,5-tetrahydro-8-methyl-1,5-benzoxazepine:

(126) 2,3,4,5-tetrahydro-8-methyl-5-nitroso-1,5-benzoxazepine (127) 5-amino-2,3,4,5-tetrahydro-8-methyl-1,5-benzoxazepine (128) 2,3,4,5-tetrahydro-8-methyl-5-[(4-piperidylidene)amino]1,5-benzoxazepine (129) 2,3,8,9,10,11-hexahydro-6-methyl-1H-pyrido[3',4':4,5]pyrrolo[1,2,3-ef][1,5]benzoxazepine

EXAMPLES 130–133

By the procedure of Example 125, the following compounds can be prepared, starting from 3,4-dihydro-8-methyl-2H-1,4-benzoxazine:

(130) 3,4-dihydro-8-methyl-4-nitroso-2H-1,4-benzoxazine (131) 4-amino-3,4-dihydro-8-methyl-2H-1,4-benzoxazine (132) 3,4-dihydro-8-methyl-4[(4-piperidylidene)amino]1,4-benzoxazine (133) 1,2,7,8,9,10-hexahydro-4-methyl-pyrido[3',4':4,5]pyrrolo[1,2,3-de][1,4]benzoxazine

EXAMPLES 134–137

By the procedure of Example 125, the following compounds can be made starting from 3,4-dihydro-2-isopropyl-2H-1,4-benzoxazine:

(134) 3,4-dihydro-2-isopropyl-4-nitroso-2H-1,4-benzoxazine (135) 4-amino-3,4-dihydro-2-isopropyl-2H-1,4-benzoxazine (136) 3,4-dihydro-2-isopropyl-4[(4-piperidylidene)amino]1,4-benzoxazine (137) 1,2,7,8,9,10-hexahydro-2-isopropyl-pyrido[3',4':4,5]pyrrolo[1,2,3-de][1,4]benzoxazine

EXAMPLES 138–140

By reacting the compounds of Examples 127, 131, and 135 with 1-methyl-4-piperidone to provide the corresponding compounds of formula II, then cyclizing according to reaction scheme A, the following compounds can be prepared:

(138) 2,3,8,9,10,11-hexahydro-6,9-dimethyl-1H-pyrido[3',4':4,5]pyrrolo[1,2,3-ef][1,5]benzoxazepine (139) 1,2,7,8,9,10-hexahydro-4,8-dimethyl-pyrido[3',4':4,5]pyrrolo[1,2,3-de][1,4]benzoxazine (140) 1,2,7,8,9,10-hexahydro-2-isopropyl-8-methyl-pyrido[3',4':4,5]pyrrolo[1,2,3-de][1,4]benzoxazine

EXAMPLES 141–147

The following compounds are prepared by a procedure similar to that described in Example 21.

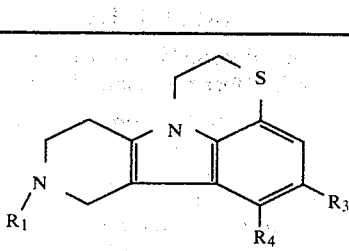

| Example No. | $R_1$ | $R_3$ | $R_4$ | Salt | M.p. |
|---|---|---|---|---|---|
| 141 | H | Cl | H | HCl | 304–305° (dec.) |
| 142 | ◁ | H | H | HCl | 246–247° (dec.) |
| 143 | H | CH$_3$ | H | HCl | 295–296° (dec.) |
| 144 | ◁ | CH$_3$ | H | HCl | 255–257° (dec.) |
| 145 | n-C$_4$H$_9$ | H | H | HCl | 259–260° (dec.) |
| 146 | (CH$_3$)$_2$CH | H | H | — | 110–112° |
| 147 | C$_2$H$_5$ | H | H | — | 98–99° |

The drugs of this invention can be administered in the usual pharmaceutical dosage forms, such as tablets, capsules, syrups, elixirs, suspensions, injectables, implants, suppositories etc. Such compositions can be described broadly as consisting essentially of a compound of formula I or salt thereof and one or more pharmaceutically acceptable vehicles or excipients. (The expression "consisting essentially of" is used to indicate that in addition to the ingredients specifically recited, i.e. the essential ingredients, the compositions can contain other ingredients, provided they do not interfere with the intended use of the compositions.) The compositions and/or method of preparation may be designed to meet the requirements of the intended dosage form.

The concentration of the active ingredient and the pharmaceutical carrier may vary for each dosage form. The ordinary range for tablets and capsules is 10–90% by weight of the active ingredient and 90–10% of the carrier. For the liquid dosage forms such as such as syrups, suspensions and injections, the concentration is ordinarily between 0.1 and 10% by weight of active ingredient and corresponding, 99.9–90% of the vehicle.

Doses of active ingredient between about 0.1 and 100 mg/kg/day can be used to induce sedation. The preferred range is 1 to 30 mg/kg/day. For those compounds which are anti-depressants, similar doses can be used to combat depression. The daily dosage can be given all at once or in intervals of from 3 to 6 hours.

Typical formulations of the type listed above which may be used for the administration of these compounds are:

EXAMPLE A

| Ingredients | mg./tablet |
|---|---|
| compound of Example 21 | 15 mg. |
| lactose, USP | 183 mg. |
| magnesium stearate, USP | 2 mg. |
| color (if desired) | q.s. |

All of the above ingredients are passed through a suitable sieve, blended for 20 minutes, and compressed directly into tablets of 200 mg. on a suitable tablet press using a 11/32" punch and die.

EXAMPLE B

| Ingredients | mg./capsule |
|---|---|
| compound of Example 37 | 25 mg. |
| lactose, USP | 100 mg. |
| magnesium stearate, USP | 1 mg. |
| colloidal silicon dioxide, N.F. | 2 mg. |

The combined ingredients are blended and passed through a 40 mesh sieve, and the mixture is encapsulated into a two-piece hard gelatin No. 3 capsule on a suitable encapsulating machine at a net weight of 128 mg.

EXAMPLE C

| Ingredients | gram/liter |
|---|---|
| Compound of Example 59 | 10 g. |
| propylparaben, USP | 0.2 g. |
| methylparaben, USP | 1.8 g. |
| sodium carboxymethylcellulose, USP (CMC) | 5 g. |
| polysorbate 80, USP | 1 g. |
| Water for Injection | q.s. to 1 liter |

The parabens, CMC and one-half of the polysorbate 80 are dissolved in about 700 ml. of Water for Injection, with agitation at 80° (solution A). A slurry is made of the active ingredient, one-half of the polysorbate 80 and about 200 ml. of Water for Injection (slurry B). Solution A is aseptically filtered through a Millipore filter to render it sterile, while slurry B is autoclaved for 30 minutes at 15 lbs. steam pressure to make it sterile. A and B are aseptically combined, brought to correct volume with sterile Water for Injection, and mixed to homogeneity.

The sedative effect of compounds of this invention is shown in the following tests:

"M.E.D."
Results given in: mg/kg po/mouse
Mouse Screen: The minimal effective dose (MED) is the lowest oral dose producing an obvious decrease in locomotor activity, using observational techniques. Groups of 3 mice are given decreasing oral doses at 0.5 log intervals (300, 100, 30 . . . etc.) until no behavioral effects are evident. Decrease of locomotor activity is indicative of general central nervous system depressant activity.

"ED$_{50}$"
Results given in: mg/kg po/mouse
Mouse Locomotor Activity Test: The ED$_{50}$ is the dose causing a 50% decrease in activity compared to animals given saline as controls. Photocell-activated cages are used to record the locomotor activity of groups of 5 animals. The mice are placed in the actophotometers 30 minutes after oral administration of saline or test compound, and locomotor activity is recorded for 1 hour. This test gives a more precise evaluation than the screen decreased above.

Results in these tests for some compounds of this invention and a standard (flurazepam) are shown in the following table.

| Compound of Example | Salt | M.E.D. | ED$_{50}$ |
|---|---|---|---|
| flurazepam | | 10 | 7 |
| 21 | HCl | 10 | — |
| 21 | lactate | 10 | — |
| 21 (65) | mesylate | 10 | 8 |
| 21 | acetate | 10 | 7 |
| 21 | — | 3 | 6 |
| 22 | HCl | 100 | 94 |
| 23 | mesylate | 30 | >100 |
| 24 | HCl | 30 | >100 |
| 26 | " | 3 | 3 |
| 27 | " | 10 | 50 |
| 28 | " | 10 | — |
| 30 | " | 30 | 12 |
| 60 | " | 10 | — |
| 36 | " | 10 | 44 |
| 37 | " | 10 | 24 |
| 31 | " | 30 | 28 |
| 32 | " | 10 | 23 |
| 33 | " | 10 | >100 |
| 35 | " | 10 | >100 |
| 34 | mesylate | 300 | — |
| 25 | HCl | 10 | 23 |
| 38 | " | 30 | >100 |
| 61 | — | 3 | 88 |
| 29 | — | >300 | — |
| 66 | mesylate | 10 | >100 |
| 64 | HCl | 10 | |
| 81 | — | >300 | |
| 41 | HCl | 10 | |
| 42 | " | 10 | |
| 95 | maleate | 10 | |
| 109 (+)-isomer | HCl | 3 | |
| 44 | " | 30 | |
| 45 | " | 3 | |
| 47 | " | 100 | |
| 48 | " | >300 | |
| 49 | " | 3 | |
| 51 | " | 100 | |
| 52 | " | 30 | |
| 40 | " | 1 | |
| 43 | " | 30 | |
| 46 | " | 100 | |
| 50 | " | 10 | |
| 117 | " | 10 | |
| 118 | " | 30 | |
| 119 | " | 30 | |
| 123 | " | 10 | |
| 124 | " | 100 | |
| 120 | " | 1 | |
| 121 | " | 100 | |
| 122 | " | 100 | |
| 110 | " | 10 | |
| 111 | " | 30 | |
| 112 | " | 10 | |
| 113 | HCl | 3 | |
| 114 | " | 10 | |
| 115 | " | 3 | |
| 125 | " | 30 | |
| 39 | " | 1 | |

Some of the compounds have antidepressant activity as well as sedative-hypnotic activity, as shown in the tetrabenazine (TBZ) antagonism test, or "anti-TBZ" test. The anti-TBZ test is a standard procedure for the detection of potential antidepressant agents.

"ED$_{50}$-Ptosis"
Results given in mg/kg. po/mouse
Anti-TBZ Test

Groups of 5 to 10 mice are given graded oral doses of a test compound. One hour after drug administration, the mice are given a subcutaneous dose of 40 mg/kg TBZ (as the mesylate). Thirty minutes after TBZ administration, each mouse is placed in the center of a circle, the diameter of which is twice the length of the mouse. Thirty seconds after the mouse is placed in the circle, two sets of readings are taken. The ability of the mouse to move out of the circle is noted and the degree of ptosis (eyelid closure) is rated on a subjective scoring system. Compounds of the imipramine type tend to reverse only the ptosis induced by TBZ. Compounds with monoamine oxidase inhibitory activity and amphetamine-like activity have been found to antagonize the ptosis and immobility induced by TBZ.

Results for compounds of this invention which have been found active in the anti-TBZ test are as follows:

| Compound of Example | Salt | $ED_{50}$-Ptosis |
|---|---|---|
| Imipramine | | 2 |
| 28 | HCl | 20 |
| 37 | " | 6 |
| 41 | " | 6 |
| 43 | " | 2 |
| 50 | " | 20 |
| 117 | " | 4.8 |
| 119 | " | 2 |
| 120 | " | 25 |
| 121 | " | 20 |

Some of the compounds of this invention, especially the hexahydro-3-substituted-1H-pyrido[3',4':4,5]pyrrolo[1,2,3-ef][1,5]benzothiazepines in which there is no substituent on the 9-position, are antibacterial, as determined in the standard microbiological test tube liquid serial dilution method*

*Bacto Brain-Heart Infusion (Cat. #0037-01-6). Difco Laboratories, Detroit, Michigan.

Microbiological Test

Ten mg of each compound are mixed with 50 ml of sterile distilled water containing 2.0 ml of dimethylformamide and one drop of Tween 80. Appropriate dilutions are made from this solution in sterile distilled water.

Test compound concentrations are made by mixing 1.0 ml of a diluted solution with 1.0 ml of sterile double-strength Bacto brainheart infusion broth** in plugged test tubes.

**Bailey, W. R., and E. G. Scott, 1962. Diagnostic Microbiology, A Textbook for the Isolation and Identification of Pathogenic Microorganisms. The C. V. Mosby Publ. Co., St. Louis, Mo., pp. 250-253.

The final test concentrations of 100 μg, 50 μg, 10 μg, 2 μg and 0.4 μg of compound per ml of culture medium are aseptically inoculated with two drops of an overnight broth culture of a test bacterium and incubated at 37° C.

After incubation for 48 hours, the test tubes are observed for signs of growth (turbidity). The lowest concentration tested which inhibits the bacterial growth (tubes remain clear) is recorded as the minimal inhibitory test concentration (M.I.T.C.).

The compounds of Examples 22, 26, 42, 44, 45 and 47 have shown antibacterial activity in the above test, especially against gram-positive organisms such as B. subtilis, Staph. aureus, and Strep. pyogenes.

I claim:

1. A compound of the formula:

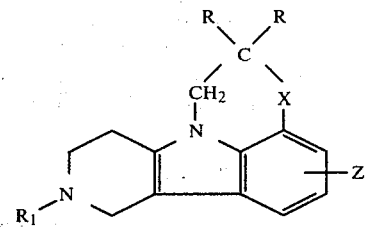

where
X is

S, or $SO_2$;

the R's are the same or different and are H, $CH_3$; or $OCH_3$; and one of them can be $C_2$-$C_9$ alkyl, phenyl, $C_7$-$C_{10}$ phenylalkyl, furyl, thienyl, pyridyl, phenyl or $C_7$-$C_{10}$ phenylalkyl substituted on adjacent ring carbon atoms with methylenedioxy, or phenyl or $C_7$-$C_{10}$ phenylalkyl substituted on the ring with 1, 2 or 3 substituents individually selected from methoxy, ethoxy, bromine, chlorine, fluorine, trifluoromethyl and $C_1$-$C_4$ alkyl;

$R_1$ is hydrogen, $C_1$-$C_4$ alkyl, $C_3$-$C_5$ alkenyl, $C_3$-$C_5$ alkynyl, $C_3$-$C_6$ cycloalkyl, $C_2$-$C_4$ alkoxycarbonyl, trifluoroacetyl or substituted $C_1$-$C_4$ alkyl where the substituent is $C_3$-$C_6$ cycloalkyl, phenyl, phenyl substituted on adjacent carbon atoms with methylenedioxy, or phenyl substituted with 1, 2 or 3 substituents individually selected from methoxy, ethoxy, bromine, chlorine, fluorine, and trifluoromethyl; and Z is H, Cl, or $CH_3$;

and their pharmaceutically suitable salts.

2. Compound of claim 1: 8-cyclopropyl-1,2,7,8,9,10-hexahydropyrido[3',4':4,5]pyrrolo[1,2,3-de][1,4]benzothiazine and its pharmaceutically suitable salts.

* * * * *